United States Patent [19]

Shafir

[11] Patent Number: 4,997,369

[45] Date of Patent: Mar. 5, 1991

[54] APPARATUS FOR DIGITIZING A THREE-DIMENSIONAL SURFACE

[75] Inventor: Aaron Shafir, Tel Aviv, Israel

[73] Assignee: Michael Knopfmacher, Grenzach-Wyhlen, Fed. Rep. of Germany; a part interest

[21] Appl. No.: 445,053

[22] Filed: Dec. 4, 1989

[30] Foreign Application Priority Data

Dec. 30, 1988 [IL] Israel .................................... 88842

[51] Int. Cl.[5] .............................................. A61C 19/04
[52] U.S. Cl. ...................................... 433/72; 128/776; 364/560; 33/503; 33/513
[58] Field of Search .................. 433/72, 75, 223, 229; 128/176, 177; 364/560, 561, 562, 563; 33/503, 504, 513, 514

[56] References Cited

U.S. PATENT DOCUMENTS

| 4,167,066 | 9/1979 | Cooper et al. | 33/504 |
| 4,192,312 | 1/1980 | Mushabac | 128/776 |
| 4,333,238 | 6/1982 | McMurtry | 33/503 |
| 4,581,826 | 4/1986 | Ernst | 33/503 |

Primary Examiner—John J. Wilson
Attorney, Agent, or Firm—Benjamin J. Barish

[57] ABSTRACT

Apparatus for digitizing the contour of a three-dimensional surface of an object includes a handle, a probe carried by the handle and movable along three independent axes to contact sample points on the three-dimensional surface, and a positional sensor for sensing the position of the handle along the three axes and for outputting positional values. The probe includes an arm deflectable during the movement of the probe, which deflections are sensed by a sensor. A digital processor processes the positional values only when one of the deflection sensors senses a deflection in its respective arm above a predetermined threshold value, and modifies the positional values by the deflection values.

18 Claims, 7 Drawing Sheets

APPARATUS FOR DIGITIZING A THREE-DIMENSIONAL SURFACE

BACKGROUND OF THE INVENTION

The present invention relates to apparatus for digitizing the contour of a three-dimensional surface. The invention is particularly applicable for digitizing a dental surface, e.g., a ground tooth for preparing a dental crown, and is therefore described below with respect to this application.

When a tooth is in an advanced state of decay, it may become necessary to apply a crown. This involves grinding the tooth and then fixing the crown to it. If one or more teeth are missing or are to be removed, it may be necessary to insert a bridge, which includes a crown applied to each of the two teeth to be bridged and integrally formed with one or more artificial teeth to fill the space of the missing tooth or teeth.

The metal infrastructure for preparing a crown or bridge is conventionally produced by making a cast model of the respective part of the oral cavity, and then using the cast model for building the crown or bridge. Such a procedure is very time-consuming and requires a large number of visits by the patient to the dentist. Moreover, this procedure is greatly dependent on the skill and experience of both the dentist and the laboratory technician in making the cast model and the crown or bridge based on it, as well as on the precision of the equipment used.

Many systems have been proposed for automatically producing crowns and bridges by digitizing the contour of the tooth to be crowned. Some of the proposed systems are based on optical measurements, as illustrated for example in U.S. Pat. Nos. 4,742,464, 4,663,720, 4,611,288 and 4,575,805. Other proposed systems are based on the use of contact-type probes which are passed over the surface of the tooth to be crowned. Examples of the latter type system are illustrated in U.S. Pat. Nos. 4,182,312, 4,478,580, 4,411,626 and 3,324,546.

U.S. Pat. No. 4,182,312 discloses a contact-type dental probe in which an aluminum tray is fixed in the patient's mouth such that when the dentist applies the probe to the patient's tooth or gum tissues, an electrical circuit is completed, via the saliva in the patient's mouth, to the tray to enable the transducer to output the positional signals of the probe. However, since the contact of the probe with the surface being digitized is based on completing an electrical circuit to the tray via the subject's saliva, the results would be distorted by the thickness of the saliva film, which is significant when compared to the precision required for dental probes of this type. U.S. Pat. No. 4,478,580 discloses apparatus for treating teeth in which a rotary cutter head is provided with stress sensors so that both the shape of the tooth being ground, as well as the resistance to grinding, are sensed during the grinding operation.

Insofar as we are aware, apparatus for digitizing the contour of a tooth in order to automatically prepare a crown or a bridge has not yet gained widespread use despite the long felt need and search for such an apparatus.

OBJECTS AND SUMMARY OF THE INVENTION

An object of the present invention is to provide improved apparatus for digitizing the contour of a three-dimensional surface, particularly a dental surface to enable dental crowns and bridges to be produced in a more efficient manner than by the present conventional techniques, and in a more precise manner than in the previously-proposed automated techniques.

According to the invention, there is provided apparatus for digitizing the contour of a three-dimensional surface of an object, comprising: a handle graspable by the user; mounting means for mounting the handle with respect to the object; a probe connected to and carried by the handle and movable thereby along three independent axes to contact sample points on said three-dimensional surface; positional sensor means for sensing the position of the handle along the three axes and for outputting positional values corresponding thereto; the probe including an arm deflectable along first and second ones of the three axes during the movement of the probe along the three-dimensional surface by the handle; first and second deflection sensor means for sensing the deflection of the arm along the first and second axes, respectively, and for outputting deflection values corresponding thereto; and a digital processor including means for processing the positional values only when one of the deflection sensors senses a deflection in its respective arm above a predetermined threshold value, and means for modifying the positional values by the deflection values to output digital surface-location values representing the location of the points on the three-dimensional surface during the movement of the probe therealong by the handle.

It will thus be seen that the deflection sensors serve the double function of: (1) determining when contact is made by the probe with the three-dimensional surface being contoured, and (2) correcting the measurements by the deflections of the probe. The apparatus thus permits three-dimensional surfaces to be digitized in an automatic and highly-precise manner. A deflection sensor for the third axis may be provided but is not essential for the above purposes.

The above-described apparatus is particularly useful for digitizing a dental surface of a subject, in which case the described mounting means includes a biting member to be clamped between the upper and lower teeth of the subject.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
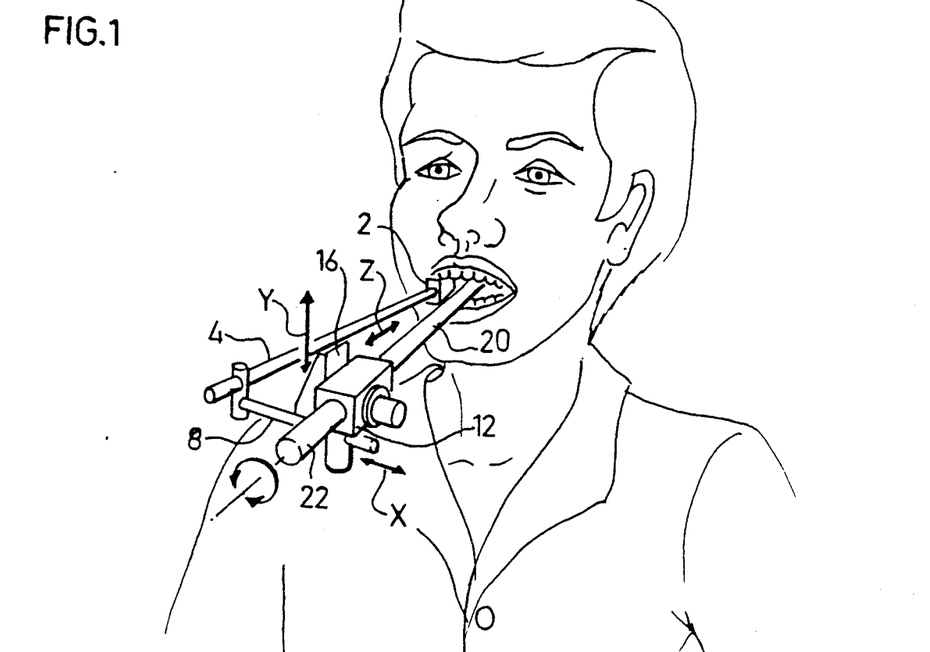
FIG. 1 illustrates one form of probe assembly constructed in accordance with the present invention for digitizing the contour of a patient's tooth.
Figure 2:
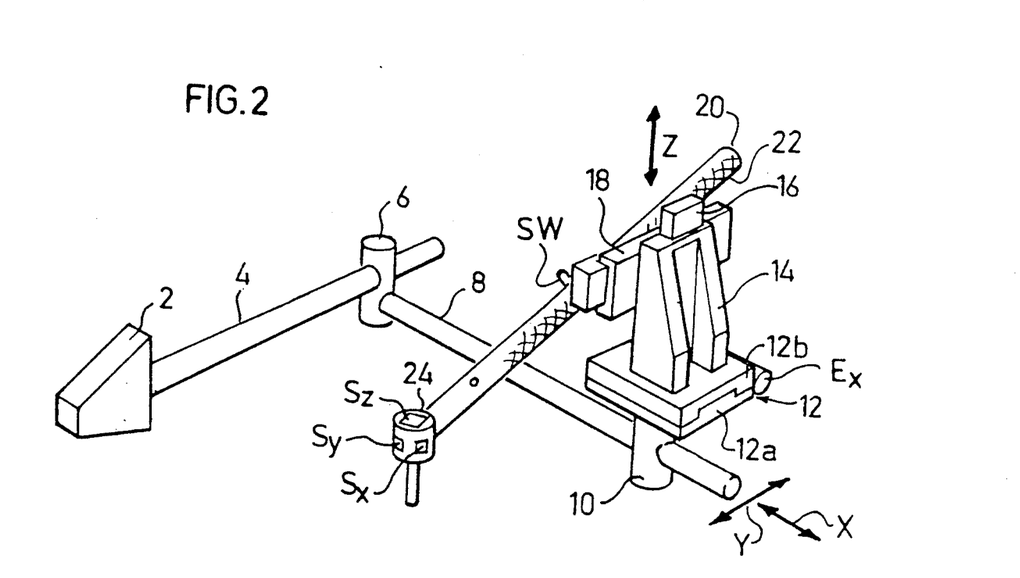
FIG. 2 is a perspective view more particularly illustrating the construction of the probe assembly.

FIGS. 1 and 2 illustrate a probe assembly constructed in accordance with the present invention for use in digitizing the contour of the surface of a tooth to receive a dental crown. After the dentist has ground the tooth as required, this probe assembly would be used with the data processor system illustrated in FIG. 8 to digitize the contour of the ground surface of the tooth in order to produce digital data for use in automatically preparing the crown according to that contour.

The probe assembly illustrated in FIGS. 1 and 2 comprises a wedge-shaped mounting member 2 to be clamped between the upper and lower teeth of the subject. Mounting member 2 is secured to one end of an arm 4 connected at its opposite end by an articulated joint 6 to one end of a second arm 8. The opposite end of arm 8 carries an articulated joint 10 to which is mounted one section 12a of a slide 12, having a second, relatively-movable section 12b to which is mounted a base member 14. Base member 14 mounts one section 16a of a further slide 16 having a second, relatively-movable section 16b which is movable perpendicularly to the direction of movement of section 12b of slide 12. Slide section 12b in turn mounts one section 18a of a third slide 18 having a second, relatively-movable section 18b movable perpendicularly to the directions of movements of both slide sections 12b and 16b. Slide section 18b in turn mounts a handle 20 knurled at one end 22 to facilitate grasping by the dentist. The opposite end of handle 20 mounts a probe head 24.

The illustrated probe assembly further includes a digitizer switch SW conveniently accessible to the dentish when probing the outer surface of the ground tooth.

Figure 5:
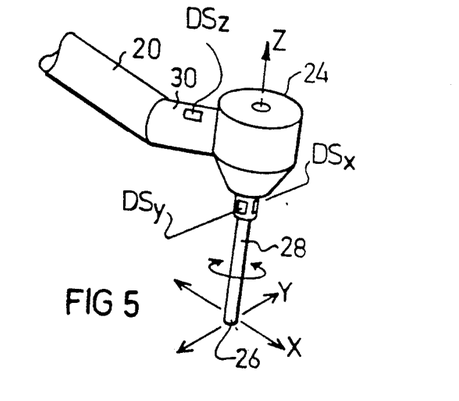
FIG. 5 illustrates the deflection sensors in the probe assembly of FIGS. 1 and 2 for sensing deflections in the three orthogonal axes.

As shown more particularly in FIG. 5, probe head 24 carries a probe 26 at the tip of an arm 28 depending from the probe head. Arm 28 is deflectable along both the X-axis and the Y-axis. A pair of deflection sensors DSx are fixed on the two opposite sides of arm 28 aligned with each other along the X-axis, and a second pair of deflections sensors DSy are fixed on the remaining two opposite sides of arm 28 aligned with each other along the Y-axis. Probe head 24 is in turn mounted to the end of handle 20 by a further arm 30 which may be deflectable along the Z-axis, and which may include a third pair of deflection sensors DSz fixed on its opposite sides aligned with each other along the Z-axis. Deflection sensors DSx, DSy, DSz may be resistance-type strain gages producing analog outputs.

Figure 3:
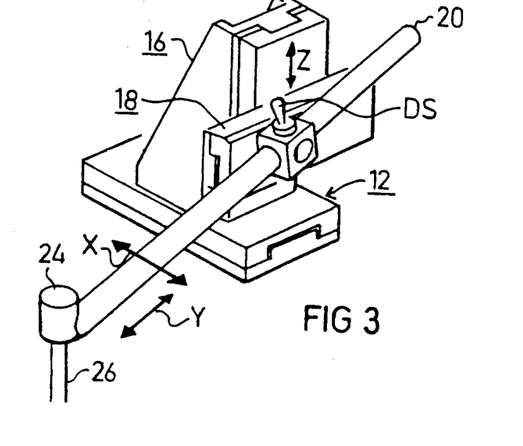
FIG. 3 is a perspective view more particularly illustrating the mounting for the handle and probe in the probe assembly.

It will thus be seen, as shown more particularly in FIG. 3, that the three slide assemblies 12, 16 and 18 permit handle 20 and probe 26 to move along the three orthogonal axes with respect to the mounting member 2. Thus, slide assembly 12 permits movement along the X-axis, slide assembly 16 permits movement along the Y-axis, and slide assembly 18 permits movement along the Z-axis.

Figure 4:
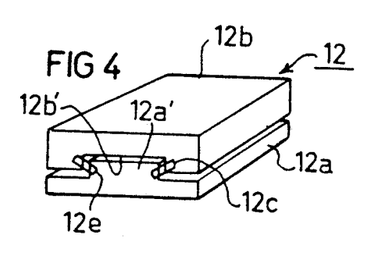
FIG. 4 illustrates the construction of one of the slides provided for each orthogonal axis in the probe assembly.

FIG. 4 more particularly illustrates the construction of slide assembly 12, it being appreciated that slide assemblies 16 and 18 are similarly constructed. Thus, slide assembly 12 includes slide member 12a fixed to joint 10 and formed with a dovetail rib 12a' received within a dove-tail groove 12b' formed in slide member 12b fixed to the common base member 14 (FIG. 2). A plurality of roller bearings 12c, e.g., of the cylindrical type, are interposed between rib 12' and groove 12b'. Such slide assemblies are well-known and permit precise movement of one of its slide members (12b, 16b, 18b) with respect to its other slide member (12a, 16a, 18a) along its respective orthogonal axis.

The probe assembly illustrated in FIG. 2 further includes a linear encoder Ex coupled to slide member 12b of slide assembly 12 outputting an electrical signal corresponding to the magnitude of movement of slide member 12b along the X-axis. The movable slide members 16b and 18b of slide assemblies 16 and 18, respectively, are similarly coupled to linear encoders Ey, Ez (FIG. 8), outputting electrical signals corresponding to the magnitude of movement of these two slide members along the Y-axis and Z-axis, respectively. The linear encoders may be potentiometers outputting analog electrical signals.

Figure 6:
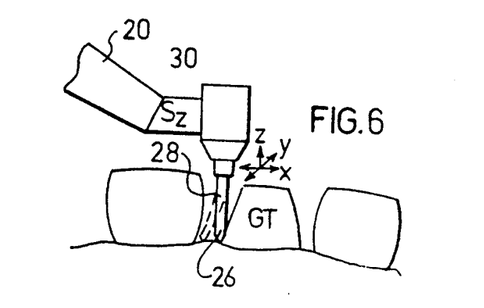
FIG. 6 illustrates the manner of using the probe assembly for digitizing the contour of a ground tooth.

FIG. 6 illustrates the manner of using the probe assembly for probing the surface of a ground tooth GT to receive a crown. During the probing operation, handle 20 is grasped by the dentist and is manipulated to cause the probe 26 to engage and move along the outer surface of the ground tooth. As soon as the probe 26 contacts the ground tooth, a deflection will be produced in its arm 28 along the X-axis and/or Y-axis, and/or in arm 30 (if included) along the Z-axis, as sensed by the deflection sensors DSx, DSy on arm 28, and DSz on arm 30. These deflections are used both for determining when the probe 26 is in contact with the ground tooth GT, and also for modifying the positional data outputted by the encoders Ex, Ey, Ez, representing the instantaneous position of handle 20 in order to compensate this positional data by the deflections produced in arms 28 and 30.

Figure 7:
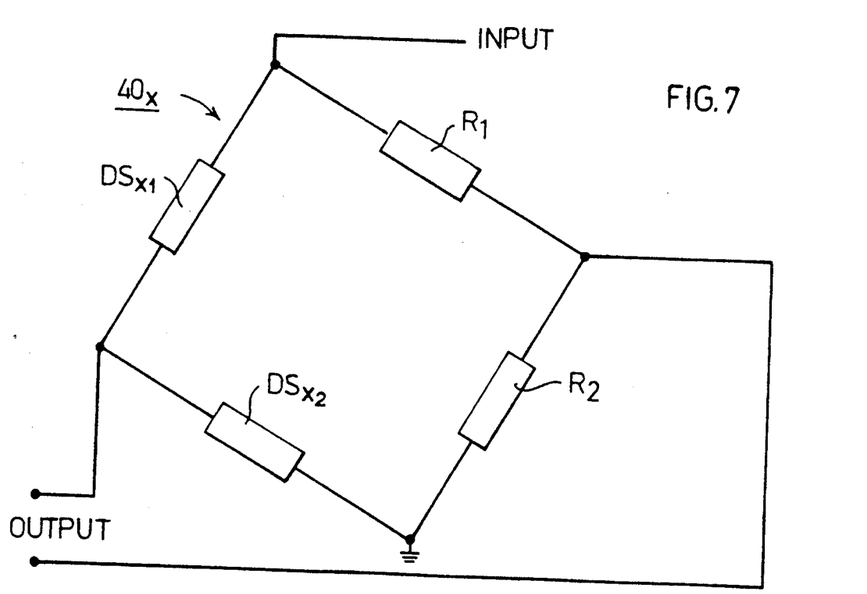
FIG. 7 illustrates a bridge circuit provided for each of the three pairs of deflection sensors in the probe assembly.

FIG. 7 illustrates a bridge circuit which may be used for each pair of the deflection sensors. While the bridge circuit of FIG. 7 illustrates the pair of deflection sensors $DSx_1$, $DSx_2$ for detecting the deflection of arm 28 along the X-axis, it will be appreciated that a similar bridge circuit may be provided for each of the other two pairs of sensors for detecting the deflection of arm 28 along the Y-axis, and Z-axis, respectively.

Thus, the circuit illustrated in FIG. 7 includes a Wheatstone bridge having four arms: two arms are occupied by resistors $R_1$, $R_2$, whereas the remaining two arms are occupied by the two deflection sensors $DSx_1$, $DSx_2$. The arrangement is such that, upon deflection of arm 28 in either direction along the X-axis, the outputs of the two deflection sensors $DSx_1$, $DSx_2$ are cumulative, thereby multiplying the sensitivity of the sensors, but the influence of temperature on the outputs of the two sensors is equal and opposite such that the bridge circuit tends to cancel temperature effects.

Figure 8:
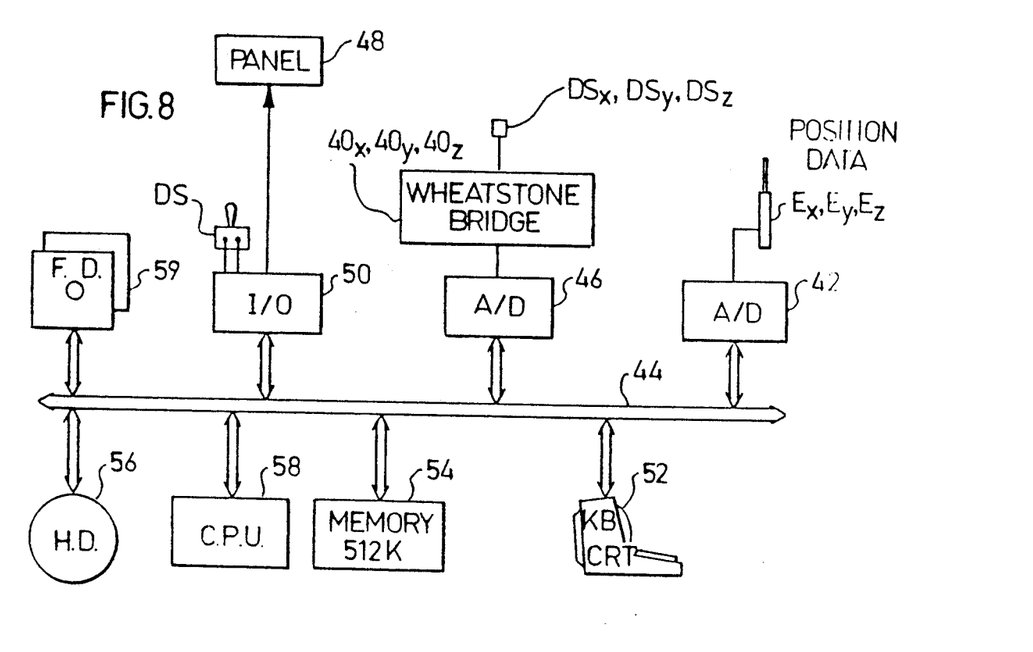
FIG. 8 is a block diagram illustrating one form of data processor system for use with the probe assembly.

FIG. 8 illustrates the main components of the data processor system for use with the probe assembly of FIGS. 1 and 2. Thus, the data processor system receives the positional data from the three linear encoders Ex, Ey, Ez, representing the instanteneous position of the handle 20, and also receives the deflection data from the three pairs of deflection sensor DSx, DSy, DSz. The deflection data is used for determining when contact of the probe 26 is made against the ground tooth GT, and also for compensating the positional data by the deflections of the two arms 28, 30 in order to produce the correct instantaneous positions of the probe 26 which define the contour of the surface of the tooth GT being probed.

Thus, as shown in FIG. 8, the positional data outputs from the three encoders, Ex, Ey, Ez are fed to an analog-to-digital converter 42 which converts the analog data to digital data before such data is transmitted to the central bus 44. Similarly, the deflection data outputs from the three pairs of deflection sensors DSx, DSy, DSz, after being processed by the Wheatstone bridge 40x, 40y, 40z for the respective sensor pair (FIG. 7), are converted to digital form in an analog-to-digital converter 46 before being transmitted to the central bus 44.

The data processor system illustrated in FIG. 8 further includes an operator panel 48 connected to the central bus 44 via an input/output unit 50. Also connected to the central bus 44 are a keyboard and display unit 52, a RAM (random-access memory) unit 54, a hard disk 56 for storing interim data, and a CPU (central processor unit) 58 controlling the overall operation of the system. The digital data outputted by the system, representing the measured sample points on the contour of the surface of the tooth to receive the crown, is outputted to one or more diskettes (floppy disks) 59, in a form to be usable in a milling machine for cutting the crown according to the contour as digitized by the illustrated system.

Figure 9:
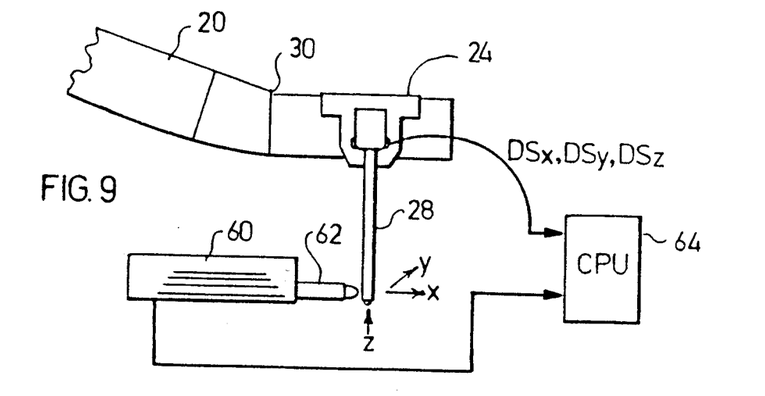
FIG. 9 illustrates the setup for precalibrating the probe assembly by producing and storing a look-up table for the respective probe assembly.

The positional data detected by the three encoders Ex, Ey, Ez are modified by the deflections in the two arms 28, 30 as sensed by the three pairs of deflection sensor DSx, DSY, DSz. These modifications are effected by means of a look-up table stored in memory unit 54 of the digital processor system which is precalibrated for the respective probe assembly to indicate the deflections corresponding to various readings of the deflection sensors. FIG. 9 illustrates a set-up which may be used for preparing this precalibrated look-up table.

As shown in FIG. 9, a precalibrating device 60 having a precisely measurable deflector element 62 is used to deflect arm 28 of the probe assembly separately along each of the three orthogonal axes. The digital positions of the delector element 62 are recorded in a computer 64 simultaneously with the outputs of the deflector sensors, to prepare a table relating the deflections, as produced and measured by deflector element 62, to the outputs of the deflection sensors DSx, DSx, DSz.

For relating the deflections to the outputs of the X-axis deflector sensors DSx, precalibrating device 60 is oriented so as to project its deflecting element 62 at precisely measured distances along the X-axis, while the readings of the deflection sensors DSx are recorded simultaneously with the instantaneous position of the deflector element 62. This procedure may be done in a continuous manner while periodically sampling, e.g., every two milliseconds, the instantaneous position of the deflector element 62 and the reading of its respective deflector sensors DSx. The same procedure would be followed also with respect to the Y-axis and the Z-axis, such that the look-up table prepared in this manner would provide precalibration data relating the outputs of all the deflector sensors DSx, DSy, DSz to the actual deflections along the three orthogonal axes.

When the apparatus is first installed and before used for digitizing the contour of a ground tooth, it is precalibrated as described above with reference to FIG. 9, in order to produced the precalibrated look-up table. This look-up table is stored in memory unit 54 of the digital processor illustrated in FIG. 8.

When the apparatus is to be used for digitizing the contour of a ground tooth GT (FIG. 6) for a particular patient, the probe assembly is attached to the patient's mouth by having the patient firmly clamp the mounting device 2 (FIG. 2) between the upper and lower teeth of the patient, with the probe handle 20 projecting outwardly of the patient's mouth, and the probe head 24 located within the patient's mouth in the general area of the ground tooth to be probed. The articulated joints 6 and 10 of the probe assembly illustrated in FIG. 2 permit manipulation of the probe handle 20 and the probe head 24 for this purpose.

The dentist, while grasping end 22 of handle 20, turns "on" the digitizer switch SW and moves the probe 26 into contact with and along the surface of the ground tooth GT (FIG. 6) so as to cover substantially its complete outer surface. During this probing operation, the three encoders Ex, Ey, Ez carried by the three slides 12, 16, 18 (FIG. 2), output positional data representing the instantaneous position of the probe handle 20; whereas the three pairs of deflector sensors DSx, DSy, DSz, output deflection data representing the deflections of probe arm 28 about the X-axis and Y-axis, and the deflections of probe arm 30 about the Z-axis. The foregoing positional data and deflection data are converted to digital form by A/D converters 42, 46 (FIG. 8) before being fed to the distribution bus 44 of the data processing system.

Preferably, the dentist first coats the tooth to be probed with a colored substance which is automatically removed where contacted by the probe. In this manner, the dentist can see whether the complete surface of the ground tooth has been probed. In any event the computer, as described below, also provides an indication whether sufficient sample points have been probed in order to reconstruct the tooth contour.

Figure 13A:
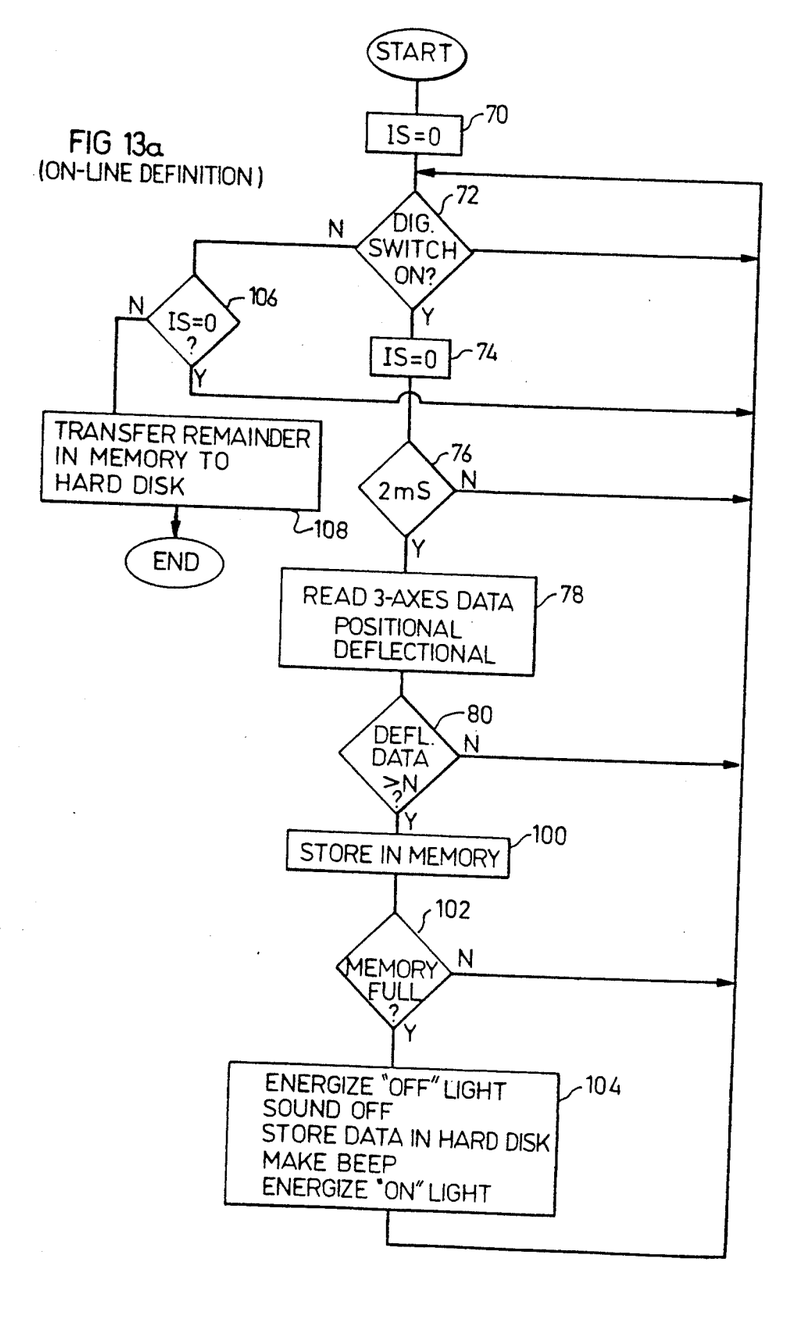
FIGS. 13a and 13b are flow diagrams illustrating another operation of the system of FIGS. 1–9, particularly when using a low-power (e.g., personal) computer, in which the digitizing operation (illustrated in FIG. 13a) is performed "on-line", and the processing operations (illustrated in FIG. 13b) are performed "off-line".

FIGS. 10–12c illustrate one mode of operation when a high-power computer is available, permitting all the operations to be performed "on-line". If, however, only a low-power computer is available, e.g., a personal computer, then the digitizing operation as illustrated in FIG. 13a may be performed "on-line", while the processing operations illustrated in FIG. 13b may be performed "off-line".

When a high-power computer is available enabling all the operations to be performed "on-line", the system operates as illustrated in FIGS. 10–12c.

Figure 10:
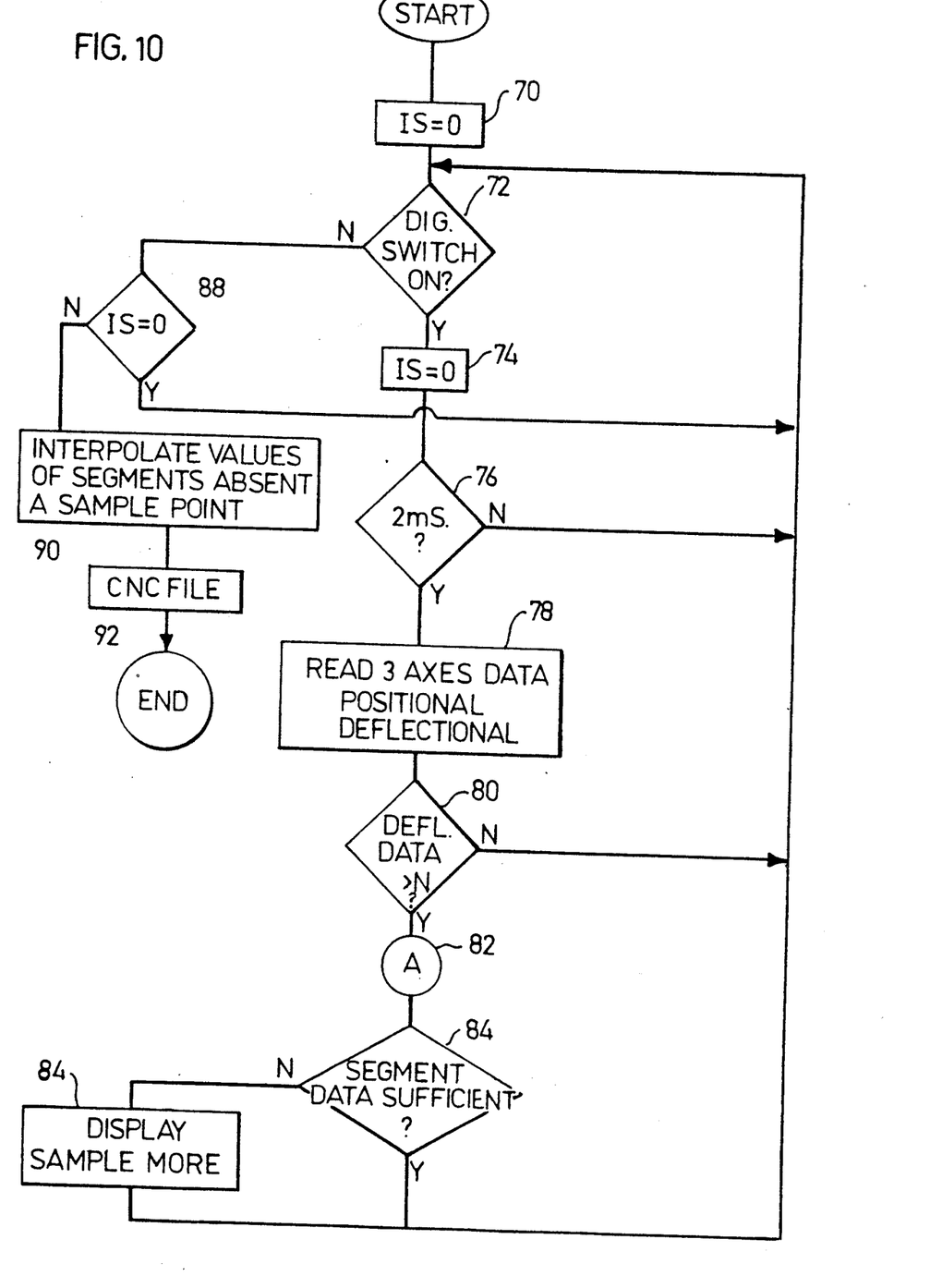
FIG. 10 is a flow diagram illustrating the operation of the system of FIGS. 1–9 where both the digitizing and processing operations are performed "on-line"

At the start, a "flag" bit (IS) is "off", i.e., IS=0 (block 70), indicating that the digitizing switch DS has not yet been actuated. During this time, the dentist may adjust the probe assembly within the patient's mouth. When the probe assembly is properly adjusted, the dentist actuates the digitizing switch SW (block 72), whereupon the "IS" flag is turned "on"; i.e., IS=1 (block 74).

As the dentist moves the probe over the ground tooth, the positional data from the three encoders Ex, Ey, Ez, and the deflection data from the three pairs of deflection sensor DSx, DSy, DSz, are collected every two milliseconds (block 76) in the distribution bus 54 (block 78), and a decision is made (block 80) whether the deflection data shows a deflection above a predetermined threshold (N) to indicate that proper contact has been made by the probe 26 with the ground tooth GT being probed. If the deflection data in all three axes is less than the predetermined threshold (N), this indicates that no proper contact has been made by the probe with the ground tooth, and therefore the collected positional data and deflection data are not stored. However, if the deflection data along any of the three axes is greater than the threshold value (N), thereby indicating that the probe tip has properly contacted the ground tooth, the collected positional data and deflection data are stored in the memory unit 54.

Figures 11, 12A, 12B, 12C:
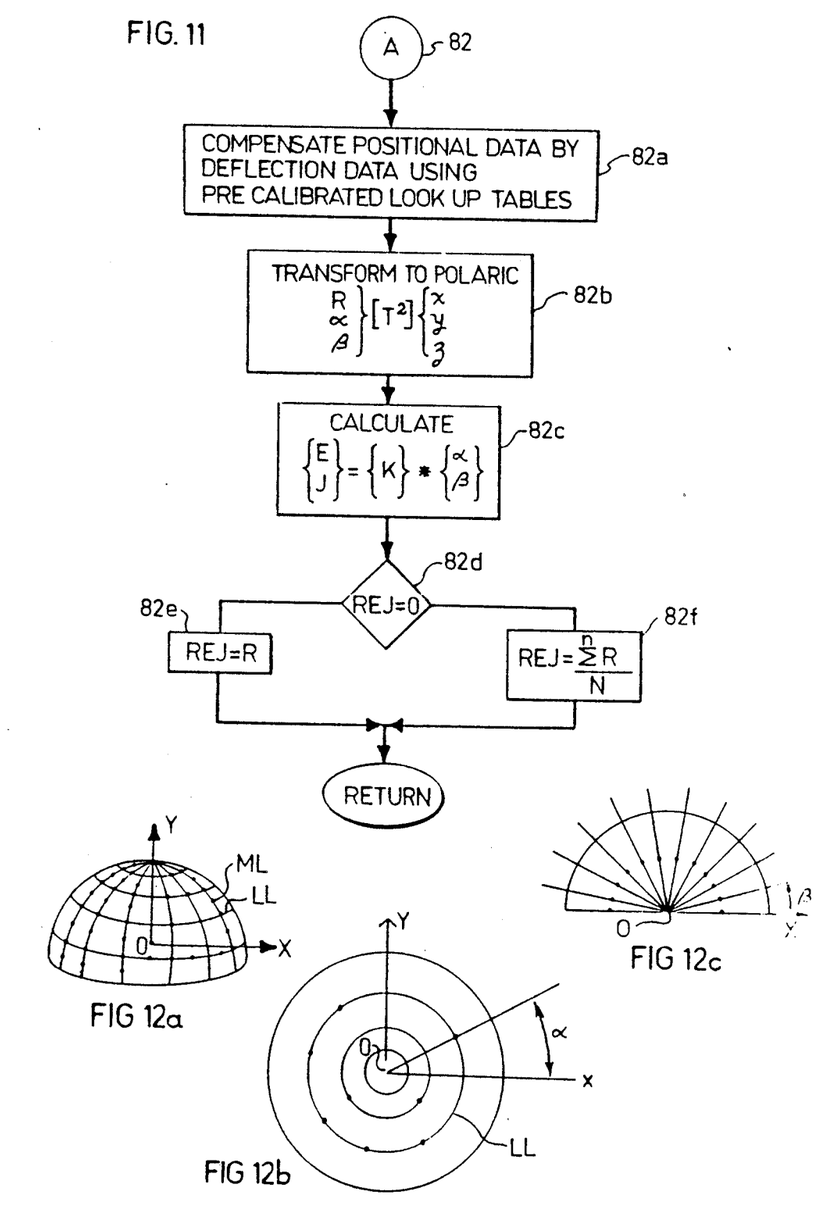
FIG. 11 is a flow diagram more particularly illustrating the compensation, transform and sort operations indicated by Routine-A in the diagram of FIG. 10.
FIG. 12a illustrates a semi-sphere geometrically divided by a plurality of longitudinal meridian lines and a plurality of horizontal latitude lines into a plurality of segments for use in defining the contour of the surface of the tooth to receive the crown.
FIG. 12b defines the X-Y plane of the semi-sphere of FIG. 12a, and particularly the manner of measuring the medidian angle "$\alpha$" in the plane of the tooth base.
FIG. 12c illustrates the X-Z plane of the semi-sphere of FIG. 12a, and particularly the manner of measuring the latitude "$\beta$" in the plane perpendicular to the tooth base.

The storing of the positional and deflection data in the memory unit 54 is effected in Routine-A (block 82) of the flow diagram of FIG. 10, and more particularly illustrated in FIG. 11. Thus, as shown in FIG. 11, the collected positional data, representing the instantaneous positions of the handle 20, is modified by the collected deflection data, representing the deflections of arms 28 and 30 when producing the positional data, in order to compensate the positional data for such deflections. This compensation (indicated by block 82a, FIG. 11) is effected by the use of the look-up table stored in the digital processor for the respective probe assembly which had been precalibrated, as described above and as illustrated in FIG. 9, to indicate the actual deflections corresponding to various outputs of the deflection sensors. The so-compensated data thus represents the instantaneous positions of the probe 28 when in contact with the tooth surface, and thereby the digital surface-location values representing surface sample points on the tooth surface.

Since the above-described probing process is done manually, the data so produced will not be in a logical array. The produced data may also be insufficient for the resolution required, which resolution may be initially inputted into the system via the keyboard 52. Accordingly, the data processor system arranges the inputted digitized data into a logical array for use in producing the data defining the digitized contour. In addition, the system checks the inputted data to see that sufficient sample points were taken to meet the required resolution for the crown to be produced.

The foregoing operations performed in Routine-A are more particularly indicated by blocks 82b–82f in FIG. 11, and by the diagrams in FIGS. 12a–12c.

As shown particularly in the diagrams of Figs. 12a–12c, the digitization space is represented by a semi-sphere which has been geometrically divided into a plurality of segments by vertically-extending meridian lines ML, and horizontally-extending latitude lines LL. The digitization space is characterized by a polar display in which each segment is defined by: (1) the angle "$\alpha$" (FIG. 12b) from the center "O" of the semi-sphere to the respective segment in the plane of the base of the tooth; and (2) the angle "$\beta$" (FIG. 12c) from the center "O" of the semi-sphere to the respective segment in the plane perpendicular to the tooth base. These segments are identified by the numbers "E" and "J". For example, "E" is the number of divisions of angle $\alpha$, and "J" is the number of divisions of angle $\beta$. Thus, segment "5-6" is the fifth segment with respect to angle $\alpha$, and the sixth segment with respect to angle $\beta$.

For each of the sample points stored in the memory as a result of the Digitization Operation, the data processor system executes a transformation to polaric as illustrated by block 82b in FIG. 11, in order to transform these stored sample points in relation to the above-described segments of the semi-spherical digitization space. Thus, the transformation process transforms the stored data, in cartesian coordinates (X, Y, Z) around the center point "O" of the tooth, to polaric coordinates, wherein each point is defined by the length "R" and the angles $\alpha$ and $\beta$ around point "O". Each point is thus identified by the distance "R" for the respective segment number ($R_{EJ}$). Such transformations are well-known, and therefore further details of the manner of producing them are not set forth herein.

Routine-A illustrated in FIG. 11 also sorts the sample points to their respective segments E, J (block 82c). As each sample is sorted to its respective segment, a check is made (block 82d) to determine whether the respective segment has yet received a sample point: if not, that sample point is recorded therein as "R" (block 82e); but if the respective segment had previously received a sample point, then the respective "R" is averaged with the previously-recorded "R's" for the respective segment (block 82f). This completes Routine-A of FIG. 11.

Returning to the flow diagram of FIG. 10, after all the sample points have been sorted to their respective segments, a check is made of all the segments to see whether there are too many unfilled segments (block 84), which could indicate that the data is sufficient according to the required resolution. For example, the required resolution, as initially inputted into the data processor system via keyboard 52, may have specified that there must be no more than two adjacent vacant segments. If the system determines that insufficient data was inputted, the system signals the dentist to sample more points (block 86), whereupon the dentist continues to scan the tooth with the probe in order to introduce additional sample point data until the "Sample More" display is extinguished.

When the "Sample More" display is extinguished, indicating to the dentist that sufficient points have been sampled, the dentish will turn-off the digitizer switch SW. This turns-off the flag "IS"; i.e., IS=0 (block 88). The system will then interpolate the values of adjacent segments which are absent a sample point in order to fill in the vacant segment or segments (block 90).

The process is completed by outputting a CNC file, e.g., to a diskette 59 (FIG. 8), representing the digitized contour of the surface of the tooth to receive the crown (block 92). This digital file may then be used for controlling a milling machine to cut the crown according to the digitized contour. The so-produced CNC file may be in a form defining the tool-path points of the milling machine to cut the digitized contour, or in a form convertible in the milling machine itself to the tool-path points of the milling machine.

The milling machine may be included in the above-described system so that the cutting of the crown can be effected immediately after the tooth surface has been digitized, thereby enabling the patient to be fitted immediately with the crown. Alternatively, the milling machine may be at another location, e.g., at a centralized dental laboratory for cutting dental crowns in accordance with CNC files supplied to it, in which case the patient would be fitted with the crown in a subsequent visit to the dentist.

Figure 13B:
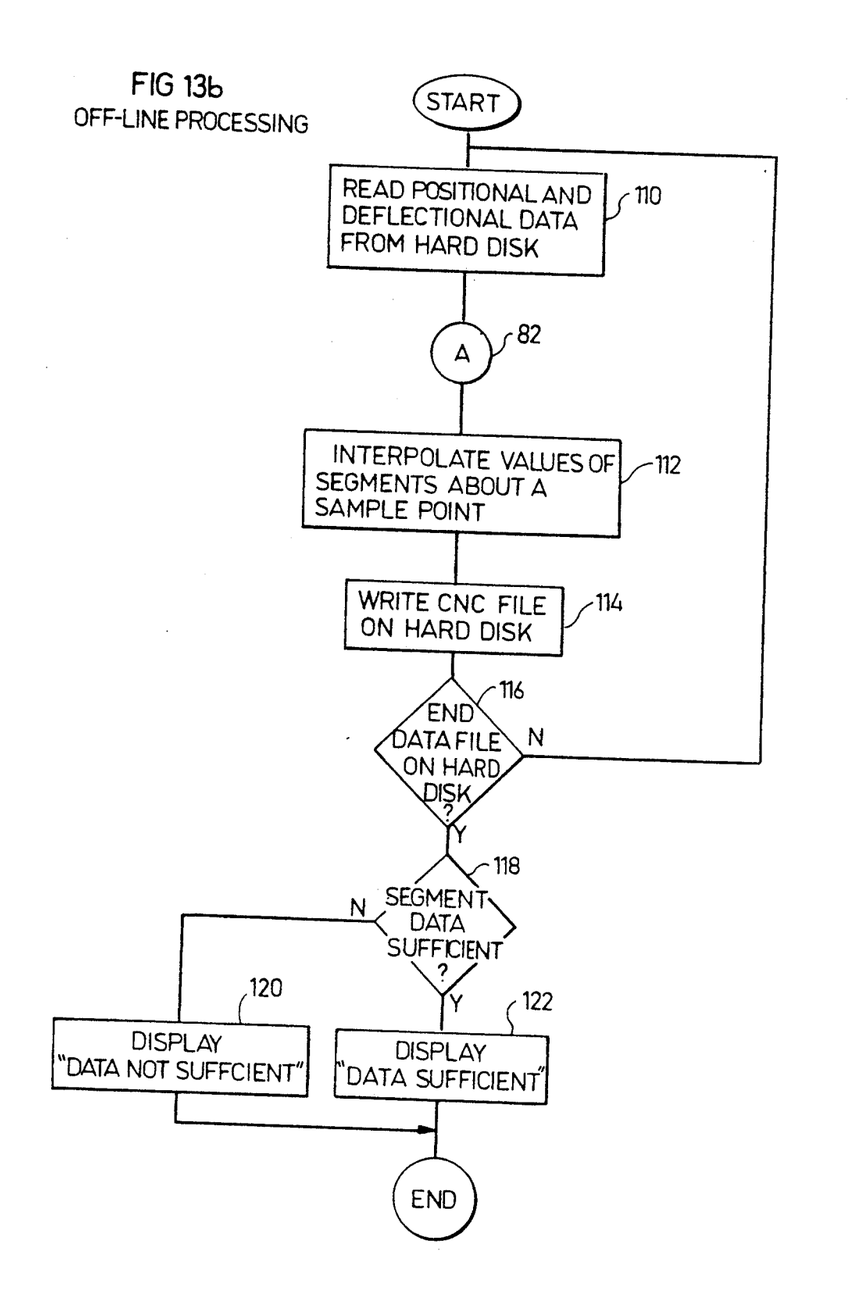

FIGS. 13a, 13b illustrate a flow diagram which may be used in order to enable the computations to be performed by a low-power computer, e.g., a personal computer, whereupon the digitizing operation (illustrated in FIG. 13a) is performed on-line, but the processing operations (illustrated in FIG. 13b) are performed off-line.

With reference to FIG. 13a illustrating the digitizing operation, the probing and data-collecting steps are the same as in the flow diagram illustrated in FIG. 10, and therefore the steps are identified by the same reference numerals 70–80. However, whereas in the FIG. 10 operation Routine-A (block 82, more particularly illustrated in FIG. 11) was entered after a decision was made that the probe had sufficient contact with the tooth, in the flow diagram illustrated in FIG. 13a following this decision the data is stored in the memory (block 100). When the memory is full, the operations illustrated by block 104 are performed, namely: the "off" light is energized; a beep is sounded, the data is stored in the hard disk; another beep is sounded; and the "on" light is energized, following which the computer returns to the beginning of the digitizing process.

This continues until the digitizing switch SW is manually turned off, whereupon flag IS is "0" (block 106), at which time all the data remaining in the memory is transferred to the hard disk (block 108). This completes the digitizing operations performed on-line.

At any time thereafter, the processing of the collected data may be done off-line, as illustrated by the flow diagram in FIG. 13b. First, the positional and deflection data are read from the hard disk (block 110), and then the computer performs the compensation, transformation and sort operations of Routine-A (block 82) as described above and as more particularly illustrated in FIG. 11. After Routine-A has been completed, the computer interpolates the values of the segments about a sample point (block 112) in the same manner as described above with respect to FIG. 10 (block 90), and the data is outputted in the form of a CNC file on the hard disk (block 114).

When the collection of the data has thus been completed on the hard disk (block 116), a decision is made, in the same manner as described above with respect to block 84 in FIG. 10, whether there is sufficient data (block 118), in which case the appropriate display (block 120 or 122) is energized. This ends the off-line processing. Should it be determined that there is insufficient data, it will be necessary for the dentist to re-examine the patient in order to complete the data obtained.

Many variations may be made in the above-described apparatus. Thus, the Z-axis sensor $DS_Z$ may be omitted since the other two sensors $DS_X$, $DS_Y$ are sufficient to sense deflection. Also, a single sensor may be provided for each axis, rather than a pair, in which case $DS_{X2}$ (FIG. 7) could be a variable resistor. Instead of using two analog-to-analog digital converters, as shown in FIG. 8 at 42 and 46, one may be used and switched-over between the two circuits. Further, instead of inputting a resolution value to determine whether sufficient points have been sampled, the sampled points can be displayed on a reproduction of the tooth involved, and it can be left to the dentist to decide whether sufficient points have been sampled to provide the required coverage. Still further, the biting teeth (2, FIGS. 1, 2) may be fixed in place by cement. The described apparatus may also be used for digitizing other surfaces or contours, in which case there may be two or more guides for each axis. Many other variations, modifications and applications of the invention will be apparent.

What is claimed is:

1. Apparatus for digitizing a dental surface of a subject, comprising:
   a handle graspable by the user;
   mounting means for mounting the handle with respect to the subject comprising a mounting member to be clamped between upper and lower teeth of the subject;
   a probe connected to and carried by the handle and movable thereby along three independent axes to contact sample points on said three-dimensional surface;
   positional sensor means for sensing the position of the handle along the three axes and for outputting positional values corresponding thereto;
   said probe including an arm deflectable along first and second ones of said three axes during the movement of the probe along the three-dimensional surface by the handle;
   first and second deflection sensor means for sensing the deflection of said arm along said first and second axes, respectively, and for outputting deflection values corresponding thereto;
   and a digital processor including means for processing said positional values only when one of said deflection sensors senses a deflection in its respective arm above a predetermined threshold value, and means for modifying said positional values by said deflection values to output digital surface-location values representing the location of the sample points on said three-dimensional surface during the movement of the probe therealong by said handle.

2. The apparatus according to claim 1, wherein said means for modifying said positional values by said deflection values comprises a look-up table stored in said digital processor and precalibrated for the respective probe to indicate the deflections corresponding to various outputs of said deflection sensor means.

3. The apparatus according to claim 1, wherein said mounting means for mounting the handle with respect to said object comprises three slides, one for each of the three axes, each slide including roller bearings to permit displacement of the handle along the respective axis of the slide.

4. The apparatus according to claim 3, wherein said positional sensor means comprises three linear encoders, one for each of said three axes and coupled to the slide of its respective axis.

5. The apparatus according to claim 4, wherein said mounting means further comprises a common base member mounting said three slides, three encoders, handle and probe.

6. The apparatus according to claim 5, wherein said mounting means further comprises a pair of articulated arms adjustably supporting said common base member, including the three slides, three encoders, handle and probe mounted thereto.

7. The apparatus according to claim 1, wherein the probe is mounted on an arm which is deflectable along the third independent axis.

8. Apparatus for enabling a user to digitize the surface of an object, comprising:
   a handle graspable by the user;
   mounting means for mounting the handle with respect to the object;
   a probe connected to and carried by the handle and movable thereby along a plurality of independent axes to contact sample points on the surface of said object;
   positional sensor means for sensing the position of the handle along the plurality of axes and for outputting positional values corresponding thereto;
   said probe including an arm deflectable along first and second ones of said axes during the movement of the probe along the surface by the handle;
   each of said deflection sensor means comprising a strain sensor fixed on a side of said deflector arm in alignment with its respective axis;
   first and second deflection sensor means for sensing the deflection of said arm along said first and second axes, respectively, and for outputting deflection values corresponding thereto;
   and a digital processor including means for processing said positional values only when one of said deflection sensors senses a deflection in its respective arms above a predetermined threshold value, and means for modifying said positional values by said deflection values to output digital surface-location values representing the location of the sample points on said surface during the movement of the probe therealong by said handle.

9. Apparatus for enabling a user to digitize the surface of an object, comprising:
   a handle graspable by the user;
   mounting means for mounting the handle with respect to the object;
   a probe connected to and carried by the handle and movable thereby along a plurality of independent axes to contact sample points on the surface of said object;
   positional sensor means for sensing the position of the handle along the plurality of axes and for outputting positional values corresponding thereto;
   said probe including an arm deflectable along first and second ones of said axes during the movement of the probe along the surface by the handle;
   said probe arm including a first pair of deflection sensors on opposite sides of the arm, and a second pair of deflection sensors on the remaining opposite sides of the arm;
   first and second deflection sensor means for sensing the deflection of said arm along said first and second axes, respectively, and for outputting deflection values corresponding thereto;
   and a digital processor including means for processing said positional values only when one of said deflection sensors senses a deflection in its respective arms above a predetermined threshold value, and means for modifying said positional values by said deflection values to output digital surface-location values representing the location of the sample points on said surface during the movement of the probe therealong by said handle.

10. Apparatus for digitizing the contour of a dental surface of a subject, comprising:
    a handle graspable by the user;
    a mounting means including a member to be clamped between the upper and lower teeth of the subject for mounting the handle with respect to the subject; a probe connected to and carried by the handle and movable thereby along three independent axes to contact sample points on said dental surface;
    positional sensor means for sensing the position of the handle along the three axes and for outputting positional values corresponding thereto;
    said probe including an arm deflectable along first and second ones of said three axes during the movement of the probe along the dental surface by the handle;
    first and second deflection sensor means for sensing the deflection of said arm along said first and second axes, respectively, and for outputting deflection values corresponding thereto;
    and a digital processor including means for processing said positional values only when one of said deflection sensors senses a deflection in its respective arm above a predetermined threshold value, and means for modifying said positional values by said deflection values to output digital surface-location values representing the location of the sample points on said dental surface during the movement of the probe therealong by said handle.

11. The apparatus according to claim 10, wherein each of said deflection sensor means comprises a strain sensor fixed on a side of said deflector arm in alignment with its respective axis.

12. The apparatus according to claim 11, wherein said means for modifying said positional values by said deflection values comprises a look-up table stored in said digital processor and precalibrated for the respective probe to indicate the deflections corresponding to various outputs of said deflection sensor means.

13. The apparatus according to claim 10, wherein said mounting means for mounting the handle with respect to said subject further comprises three slides, one for each of the three axes, each slide including roller bearings to permit displacement of the handle along the respective axis of the slide.

14. The apparatus according to claim 13, wherein said positional sensor means comprises three linear encoders, one for each of said three axes and coupled to the slide of its respective axis.

15. The apparatus according to claim 14, wherein said mounting means further comprises a common base member mounting said three slides, three encoders, handle and probe.

16. The apparatus according to claim 15, wherein said mounting means further comprises a pair of articulated arms adjustably supporting said common base member, including the three slides, three encoders, handle and probe mounted thereto.

17. The apparatus according to claim 10, wherein the probe is mounted on an arm which is deflectable along the third independent axis.

18. The apparatus according to claim 10, wherein said probe arm includes a first pair of deflection sensors on opposite sides of the arm, and a second pair of deflection sensors on the remaining opposite sides of the arm.

* * * * *